United States Patent
Shi et al.

(10) Patent No.: US 12,023,072 B2
(45) Date of Patent: Jul. 2, 2024

(54) ANTERIOR CERVICAL PLATE, INTERNAL FIXATION SYSTEM FOR USE IN ACAF AND APPLICATION THEREOF

(71) Applicant: Shanghai Changzheng Hospital, Shanghai (CN)

(72) Inventors: Jiangang Shi, Shanghai (CN); Dan Han, Shanghai (CN)

(73) Assignee: SHANGHAI CHANGZHENG HOSPITAL, Shanghai (CN)

( * ) Notice: Subject to any disclaimer, the term of this patent is extended or adjusted under 35 U.S.C. 154(b) by 0 days.

(21) Appl. No.: 17/791,828

(22) PCT Filed: Jun. 13, 2022

(86) PCT No.: PCT/CN2022/098485
§ 371 (c)(1),
(2) Date: Jul. 8, 2022

(87) PCT Pub. No.: WO2023/065689
PCT Pub. Date: Apr. 27, 2023

(65) Prior Publication Data
US 2024/0173054 A1 May 30, 2024

(30) Foreign Application Priority Data
Oct. 18, 2021 (CN) .......................... 202111210904.3

(51) Int. Cl.
*A61B 17/70* (2006.01)
(52) U.S. Cl.
CPC ...... *A61B 17/7059* (2013.01); *A61B 17/7082* (2013.01)
(58) Field of Classification Search
CPC ............ A61B 17/7059; A61B 17/8004; A61B 17/8061; A61B 17/80; A61B 17/8014; A61B 17/8019
See application file for complete search history.

(56) References Cited

U.S. PATENT DOCUMENTS

2005/0137597 A1* 6/2005 Butler ................ A61B 17/8042
606/281
2007/0123879 A1* 5/2007 Songer ............... A61B 17/8047
606/288
(Continued)

FOREIGN PATENT DOCUMENTS

CN 202027693 U 9/2011
CN 109044572 A 12/2018
(Continued)

OTHER PUBLICATIONS

PCT/CN2022/098485, International Search Report dated Aug. 29, 2022, 5 pages—Chinese, 4 pages—English.
(Continued)

*Primary Examiner* — Eduardo C Robert
*Assistant Examiner* — Michelle C Eckman
(74) *Attorney, Agent, or Firm* — Andrew F. Young; NOLTE LACKENBACH SIEGEL

(57) ABSTRACT

The invention relates to an anterior cervical plate, a lifter and an internal fixation system for use in ACAF. Fusion windows are formed at a head end and a tail end of the anterior cervical plate, wherein each of the fusion windows has a width of more than 8 mm, and a height of more than 10 mm. At least one elongated lifting groove is provided at a central longitudinal axis. It further comprises an auxiliary plate which covers a front side of the plate body when in use. The lifter comprises a lifting nail and a screwdriver. The lifting nail has a first travel control body and a second travel control body. The screwdriver is provided with a screwdriver sleeve head sleeved outside of the second travel control body and making the screwdriver to rotate with it. The internal fixation system comprises the anterior cervical plate and the lifter.

9 Claims, 7 Drawing Sheets

(56) References Cited

U.S. PATENT DOCUMENTS

| | | | |
|---|---|---|---|
| 2007/0123884 A1* | 5/2007 | Abdou | A61B 17/8033 |
| | | | 606/279 |
| 2015/0230841 A1* | 8/2015 | Freese | A61B 17/86 |
| | | | 606/279 |
| 2016/0235453 A1* | 8/2016 | Biedermann | A61B 17/8061 |
| 2020/0146839 A1* | 5/2020 | Shi | A61B 17/7001 |
| 2021/0077165 A1 | 3/2021 | Cordaro et al. | |

FOREIGN PATENT DOCUMENTS

| | | | | |
|---|---|---|---|---|
| CN | 109288571 A | 2/2019 | | |
| CN | 209645044 U | 11/2019 | | |
| CN | 213249614 U | 5/2021 | | |
| CN | 113786234 A | 12/2021 | | |
| CN | 216021331 U | 3/2022 | | |
| FR | 3009678 A1 * | 2/2015 | | A61B 17/1728 |
| WO | WO-2017197317 A1 * | 11/2017 | | A61B 17/70 |

OTHER PUBLICATIONS

PCT/CN2022/098485, Written Opinion dated Aug. 29, 2022, 7 pages—Chinese, 7 pages—English.

* cited by examiner

ANTERIOR CERVICAL PLATE, INTERNAL FIXATION SYSTEM FOR USE IN ACAF AND APPLICATION THEREOF

CROSS REFERENCE TO RELATED APPLICATIONS

This application relates to and claims priority as a § 371 national phase, from PCT/CN2022/098485 filed Jun. 13, 2022, the entire contents of which are incorporated herein by reference, which in turn claims priority to CN 202111210904.3 filed Oct. 18, 2021.

BACKGROUND OF THE INVENTION

1. Field of the Invention

The invention relates to the technical field of medical apparatus and instruments, and more particularly, to an anterior cervical plate, an internal fixation system for use in ACAF and an application thereof.

2. Description of the Related Art

The anterior approach is one of the commonly used surgical approaches for the cervical spine, and it is widely used in cervical degenerative diseases, trauma, deformities, tumors and other diseases. Anterior cervical plate internal fixation system can provide strong fixation and is now commonly used in anterior cervical spine surgery. The clinical plate internal fixation system consists of a plate and a plurality of screws. The plate are available in a variety of types according to locking ways for the screws, static compression or dynamic compression. Regardless of the existing type of plate, since an observation hole for bone grafting of the plate is small, the method is to place a fusion cage or a bone graft first, and then place the plate for fixation.

Cervical spine anterior controllable antedisplacement and fusion (ACAF) surgery is first initiated by the inventor of the invention, Shi Jiangang, a professor. It is an emerging technology of anterior cervical spine in recent years. It has advantages of high safety and excellent nerve recovery. It is especially suitable for long segments, severe posterior longitudinal ligament ossification or spinal stenosis caused by other reasons. Therefore, ACAF is receiving a lot of attention from all walks of life. During the operation, the anterior cervical plate/screws are used as a "suspension bridge" to move the cervical vertebra and the compression object forward as a whole.

The current technical problem is that the conventional anterior plate used in OPLL disease cannot realize the ACAF technical concepts, that is, it is impossible to achieve a precise lifting of the compression object, maintenance of the intervertebral physiological height and restoration of the ideal physiological curvature of the cervical spine. Reasons for such problems are as follows: 1. when using the conventional anterior cervical plate, the fusion cage needs to be placed first, and then the lifting operation is performed. After the fusion cage is placed, it may be clamped with the residual vertebra, which will affect the subsequent advancement operation. Such a phenomenon is quite obvious in the intervertebral space between an upper end and a lower end. 2. When using the "suspension bridge" principle to move forward, the conventional anterior cervical plate needs screws to be screwed into screw holes on both sides. Unbalanced force applied on the two sides may lead to the rotation of the remaining vertebra, thereby affecting the effect of forward movement, and even causing neurological complications. All of this leads to a less obvious effect of the conventional anterior plate in restoring the physiological curvature of the cervical spine during surgery. In addition, it has difficulty in restoring the physiological curvature during the surgery, or even the physiological curvature may lose after the surgery.

A patent application CN 109288571A previously submitted by the present applicant provides a natural height fixing plate for cervical vertebra. The natural height fixing plate is provided with a plate body, wherein the plate body is provided with a fusion window, a locking member and a screw fixing hole matched with a screw, the minimum distance between upper and lower side walls of the fusion window in the vertical axial direction is 3-8 mm, and the minimum distance between left and right side walls of the fusion window in the horizontal axial direction is 12.1-18 mm. The natural height fixing plate of the cervical vertebra is used in the cervical discectomy. In the long-term clinical work, the inventor finds that a height of a bone grafting fusion cage itself is larger than a height of the intervertebral disc to ensure extrusion with adjacent vertebrae and promote osteogenesis. However, it will cause upper and lower vertebrae to be stretched out. If several intervertebral discs are removed, a plurality of segments will be stretched too much. As a result, the cervical spine may lose its natural height, leading to some surgical complications such as pain neck. Therefore, the fusion window of the fixing plate is large enough to allow the fusion cage to pass through. After the intervertebral disc is removed during the operation, the vertebra is fixed first and then the fusion cage is implanted, thereby avoiding the problem that the neck aches due to the fact that the natural height is lost due to excessive stretching of the vertebra caused by the implantation of the fusion cage.

A patent application CN 109044572A previously submitted by the present applicant provides a lifting tool for cervical vertebra forward-movement fusion. The lifting tool comprises a lifting fixing body, a travel control body, a connecting rod, a movable handle and a fixed handle. One end of the travel control body is connected with the lifting fixing body, the other end of the travel control body is connected with the connecting rod; the movable handle is arranged on a peripheral surface of the connecting rod and is movably connected with the connecting rod. The fixed handle is arranged at one end of the connecting rod; the travel control body is provided with an external thread, the movable handle is provided with an internal thread, and when the internal thread on the movable handle is matched with the external thread on the travel control body for screwing, the travel control body and the movable handle produce relative motions. The lifting tool for cervical vertebra forward-movement fusion has the advantages that the tool can achieve a controllable, vertical, and stable lifting of the cervical vertebra.

However, we are now in an urgent need of an anterior cervical plate and an internal fixation system suitable for use in ACAF. Such cervical plate and the internal fixation system are capable of implement ACAF technical concepts of precisely lifting a compression object, maintaining an intervertebral physiological height, and restoring the ideal physiological curvature of the cervical spine.

SUMMARY OF THE INVENTION

A first object of the invention is to overcome disadvantages in the prior art and provides an anterior cervical plate suitable for use in ACAF. Such cervical plate is capable of implement technical concepts of precisely lifting a compression object, maintaining an intervertebral physiological height, and restoring the ideal physiological curvature of the cervical spine.

A second object of the invention is to overcome disadvantages in the prior art and provides an internal fixation system suitable for use in ACAF. The internal fixation system comprises the above-mentioned anterior cervical plate and a lifter which facilitates a stable lifting of the compression object in ACAF and effectively avoids damage to the vertebrae.

A third object of the invention is to overcome disadvantages in the prior art and provides an application of the internal fixation system in ACAF. In this way, a precise, controllable, stable and safe lifting of the compression object can be achieved, and surgical effects can be greatly improved.

In order to achieve the first objected as mentioned above, the invention adopts the following technical solution:
- an anterior cervical plate for use in ACAF, wherein, the anterior cervical plate having a plate body and a screw fixing hole, fusion windows are formed at a head end and a tail end of the plate body, each of the fusion windows has a width of more than 8 mm, and a height of more than 10 mm; at least one elongated lifting groove is provided at a central longitudinal axis of the plate body, a lengthwise direction of the at least one elongated lifting groove is consistent with a lengthwise direction of the plate body.

As a preferred embodiment of the invention, the anterior cervical plate for use in ACAF further comprises an auxiliary plate, the auxiliary plate covers a front side of the plate body when in use and exposes to the fusion windows, the lifting groove of the plate body, and the screw fixing hole, and the auxiliary plate is fixed to the plate body.

More preferably, the auxiliary plate is fixed to the plate body with screw, with bayonet, or by riveting; the auxiliary plate has the same shape as the plate body.

As another preferred embodiment of the invention, the number of the lifting groove is 1, the fusion window at the head end, the fusion window at the tail end and the lifting groove are in communication with one another.

As another preferred embodiment of the invention, the number of the lifting groove is 2 or greater than 2, the fusion window at the head end communicates with a lifting groove close to the head end, the fusion window at the tail end communicates with a lifting groove close to the tail end, and the lifting grooves do not communicate with each other.

As another preferred embodiment of the invention, the screw fixing hole comprises an end screw fixing hole and a side screw fixing hole, the end screw fixing hole is fixed at the head and tail ends of the plate body, the side screw fixing hole is fixed on left and right sides of the lifting groove.

More preferably, the fusion window at the head end is located below the end screw fixing hole at the head end, and the fusion window at the tail end is located above the end screw fixing hole at the tail end.

More preferably, the side screw fixing holes on left and right sides of the lifting groove are arranged symmetrically with each other.

As another preferred embodiment of the invention, the plate body is made of stainless steel, silicon steel, carbon steel, titanium alloy, pure titanium, cobalt-nickel alloy or a polymer material.

In order to achieve the second objected as mentioned above, the invention adopts the following technical solution:
- an internal fixation system for use in ACAF, comprising the above-mentioned anterior cervical plate and the lifter for use in ACAF.

The lifter comprises a lifting nail and a screwdriver; the lifting nail is provided with a lifting fixation body, a first travel control body, a mounting joint and a second travel control body, the second travel control body is sleeved outside of the first travel control body, and the second travel control body is provided with an internal thread matching with an external thread of the first travel control body, an axial groove is molded on an outer surface of the second travel control body; the screwdriver is provided with a screwdriver handle, a screwdriver extension rod and a screwdriver sleeve head, an interior of the screwdriver sleeve head is provided with an groove matching with the groove of the second travel control body.

In order to achieve the third objected as mentioned above, the invention adopts the following technical solution:
- an application of the internal fixation system for use in ACAF comprising the steps of:
  Step 1, preoperative preparation, including measuring a thickness of an ossific mass;
  Step 2, making an incision according to the length of a surgical segment and the condition of a patient's neck to expose relevant vertebral bodies;
  Step 3, for the treatment of intervertebral space in a lifting segment, only posterior longitudinal ligament needs to be exposed, and for the treatment of intervertebral space at head and tail ends, the posterior longitudinal ligament of the intervertebral space is removed to expose endorachis;
  Step 4, removing a bone in a front part of the vertebra according to a respective thickness of the ossific mass of each segment;
  Step 5, slotting opposite sides of each vertebra in the lifting segment, and then placing a prebent anterior cervical plate used in ACAF with an appropriate length on an anterior edge of the vertebra, installing vertebral screws on the end screw fixing holes at the head and tail ends of the plate body at a head and tail vertebra outside of the lifting segment; in the lifting groove, screwing the lifting nail on a pre-lifted vertebra;
  Step 6, slotting on the same side of each vertebra in the lifting segment;
  Step 7, fitting a screwdriver over the lifting nail, turning the screwdriver handle until each vertebra in the lifting segment fits into the plate body; and
  Step 8, inserting a fusion cage or a bone graft in the intervertebral space at the head and tail ends near the lifting segment outside the lifting segment through the fusion window, and performing bone grafting in grooves on both sides of each vertebra in the lifting segment, performing hemostasis, closing the incision, and postoperative braking.

As another preferred embodiment of the invention, when it is desired to install a cervical fusion cage between the intervertebral space between the lifting segments, it is necessary to measure a size of each intervertebral space according to a trial model, the cervical fusion cage is installed in the intervertebral space between the lifting segments, and a prebent anterior cervical plate with an appropriate length for use in ACAF is placed on an anterior edge of the vertebra.

The present invention has the following advantages:
1. The head and tail ends of the plate body are provided with enlarged fusion windows. The vertebra can be moved forward first, and then the intervertebral fusion cage can be inserted to ensure the effect of the forward movement of the vertebra, to the greatest extent.

2. The lifting groove is located in the center of the plate body, which avoids the phenomenon of rotation during the lifting process of the pressure-inducing reduction body, and the lifting groove is a longitudinal strip, which can be lifted at any position to achieve precise and controllable decompression.

3. It is equipped with the auxiliary plate to ensure strength, which is conducive to the correction of the physiological curvature during the operation and ensures the best recovery of the physiological curvature of the cervical vertebra.

4. The fusion windows are only arranged at the head and tail ends for fusion of the posterior intervertebral fusion cages at the head and tail ends outside of the lifting segment. The fusion cages or the bone grates are first inserted into the intervertebral space between the vertebrae in the lifting segment, which does not affect the precise lifting of the vertebra and ensures the overall strength of the plate.

5. The lifter consists of two parts: a lifting nail and a screwdriver. The longer screwdriver drives the second travel control body to lift the vertebra, which is conducive to the smooth lifting of the vertebra. In addition, force is more evenly applied to the plate, damage to the vertebra from the surgery can be possibly avoided, to the greatest extent.

Generally, the anterior cervical vertebra and the lifter for use in ACAF, that is, a whole internal fixation system can implement ACAF technical concepts—height of physiological intervertebral space, and decompression of lifting compression complex is precisely controllable, the optimal physiplogical curve is restored. In this way, the operation can be carried out in a more simplified, reliable and precise way, complications can be reduced, surgical risks are reduced, and surgical effects are improved.

DETAILED DESCRIPTION

Figure 1:
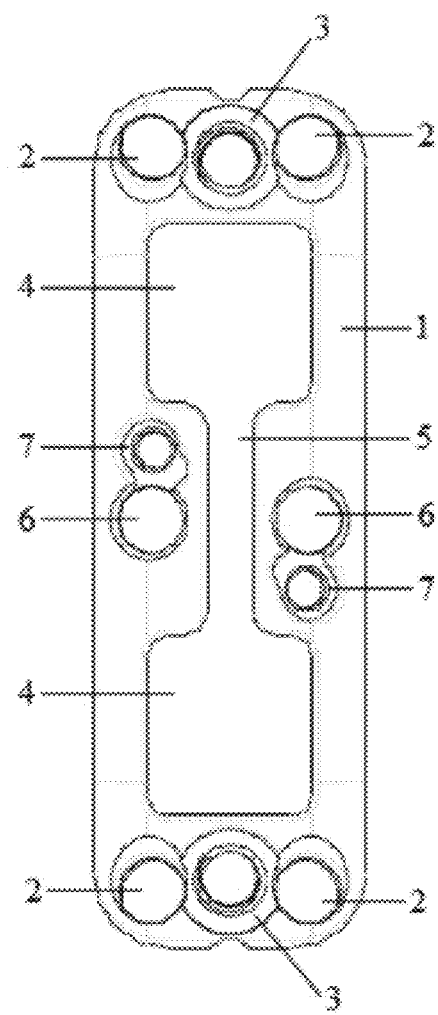
FIG. 1 is a front view of an anterior cervical plate for use in ACAF in a first embodiment of the invention.

The present invention will now be described fully hereinafter with reference to the accompanying drawings.

Reference numerals and components involved in the figures are listed as follows:
1 plate body
2 end screw fixing hole
3 end screw locking element
4 fusion window
5 lifting groove
6 side screw fixing hole
7 side screw locking element
8 auxiliary plate
82 end screw fixing hole viewing window
83 end screw locking element viewing window
84 fusion window viewing window
85 lifting groove viewing window
86 side screw fixing hole viewing window
87 side screw locking element viewing window
88 second locking element
9 first locking element
11 lifting nail
111 lifting fixation body
112 first travel control body
113 mounting joint
114 second travel control body
1141 groove
12 screwdriver
121 screwdriver handle
122 screwdriver extension rod
123 screwdriver sleeve head Example 1

Figure 2:
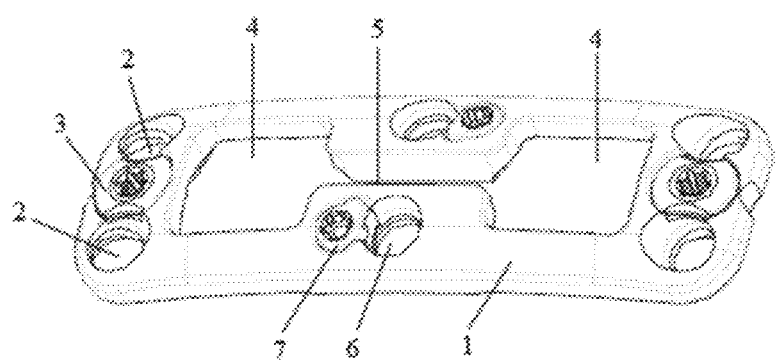
FIG. 2 is a perspective view of the anterior cervical plate for use in ACAF in a first embodiment of the invention.

Referring to FIGS. 1 and 2. FIG. 1 is a front view of an anterior cervical plate for use in ACAF in a first embodiment of the invention, and FIG. 2 is a perspective view of the anterior cervical plate for use in ACAF in the first embodiment of the invention.

The anterior cervical plate for use in ACAF is provided with a plate body 1. The plate body 1 is provided with two end screw fixing holes 2 at its head and tail ends respectively. The two end screw fixing holes 2 are arranged at left and right sides, respectively, and an end screw locking element 3 is provided therebetween. The plate body 1 is further provided with two rectangular fusion windows 4. One of the two fusion windows 4 is located below the end screw fixing hole 2 at the head end of the plate body 1, and the other fusion window 4 is located above the end screw fixing hole 2 at the tail end of the plate body 1. The minimum distance (length) between upper and lower side walls of the fusion window 4 in the vertical axial direction is 10 mm, and the minimum distance (width) between left and right side walls of the fusion window 4 in the horizontal axial direction is 8 mm. The plate body 1 is further provided with a lifting groove 5. The lifting groove 5 is an elongated groove. A lengthwise direction of the elongated lifting groove is consistent with a lengthwise direction of the plate body 1. The lifting groove 5 has a width in a range from 3 mm to 6 mm, and a length in a range from 10 mm to 20 mm. The lifting groove 5 communicates with the two fusion windows at the head and tail ends to forms a " I " shape. Left and right sides of the lifting groove 5 is each provided with a side screw fixing hole 6, and each side screw fixing hole 6 is provided with a side screw locking element 7. The side screw fixing holes 6 and the side screw locking elements 7 on the left and right sides are symmetrically distributed.

The anterior cervical plate for use in ACAF in this example can be customized according to the strength of the plate and a physiological structure of a patient. One example of a specification of the anterior cervical plate is as follows: the plate body 1 has a thickness of 3.5 mm, a length of 51 mm, and a width of 16 mm. A central axis of the end screw fixing hole 2 at the head end is inclined 20° toward the head end, and a central axis of the end screw fixing hole 2 at the tail end is inclined 20° toward the tail end. A central axis of each end screw fixing hole 2 is inclined inwardly by 6°.

The anterior cervical plate for use in ACAF in this embodiment is suitable for the case of lifting a single vertebra.

Figure 12:
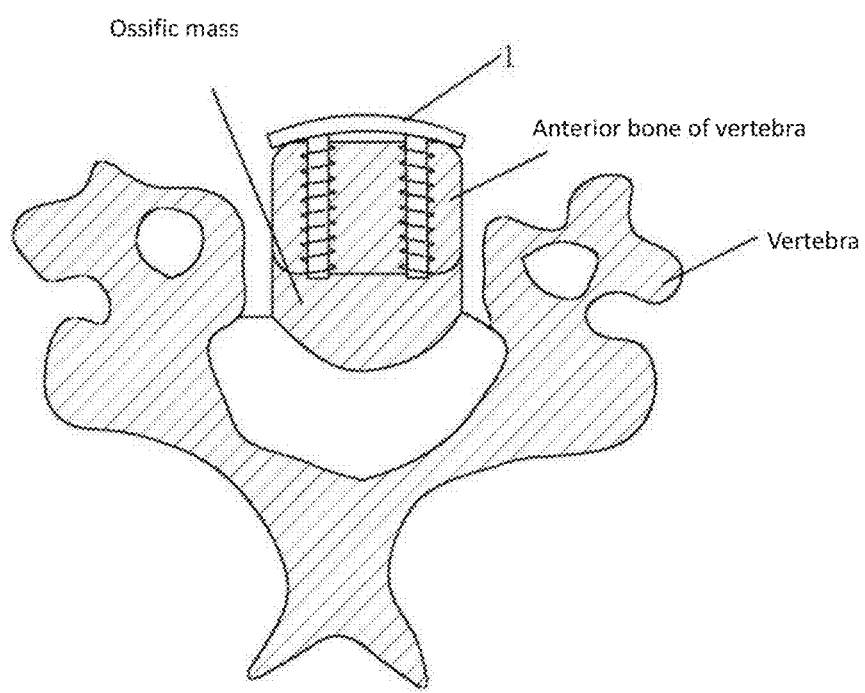
FIG. 12 is a longitudinal sectional view of a vertebra after grooves are formed on both sides of the vertebra.

A method for using the anterior cervical plate for use in ACAF in this embodiment comprises;

1. preoperative preparation: fully evaluating the frontal and lateral position, hyperextension and flexion position of the cervical spine, and perform tracheal movement training; taking detailed measurements of the ossific mass thickness, anteroposterior diameter of the vertebra, cervical curvature, ossific mass width, intervertebral space height and location of the spinal cord by imaging techniques;
2. a patient is under general anesthesia and he/she is in the supine position; a transverse incision or a longitudinal incision is selected according to the length of the surgical segment and the condition of the patient's neck, and the incision is made to expose relevant vertebrae;
3. treatment of intervertebral space: for the treatment of intervertebral space in a lifting segment, only posterior longitudinal ligament needs to be exposed, and for the treatment of intervertebral space at head and tail ends, the posterior longitudinal ligament of the intervertebral space is removed to expose endorachis;
4. removing a bone in a front part of the vertebra according to a thickness of the ossific mass measured by imaging techniques;

a thickness of the removed bone at the front part of the vertebra is theoretically the same as a thickness of the ossific mass at the rear part of the vertebra; when the ossification thickness exceeds 6 mm, the lifting distance can be further increased by using a curved titanium plate;

5. slotting opposite sides (the opposite side refers to a side away from a surgeon) of each vertebra in the lifting segment, and then placing a prebent anterior cervical plate used in ACAF with an appropriate length on an anterior edge of the vertebra, installing vertebral screws on the end screw fixing holes 2 at the head and tail ends of the plate body 1 at a head and tail vertebra outside of the lifting segment; please note that screw tails of the vertebral screws are screwed until they fit against the plate body 1; in the lifting groove, screwing the lifting nail 11 on a pre-lifted vertebra;

slotting on the opposites is as follows: using the forefoot of the uncinate process as an anatomical landmark of the longitudinal osteotomy, selecting an area at a distance of 1 mm from the ossified material as the slotting boundary, after reaching the cortex of the posterior wall of the vertebra, use a laminectomy rongeur to remove the posterior wall of the remaining vertebra at the bottom of the groove;

6. slotting on the same side (the same side refers to a side close to the surgeon) of each vertebra in the lifting segment in a way as the slotting on the opposite sides, and moving on to the next step after both sides are slotted (as shown in FIG. 12);
7. forward movement of the vertebral ossification complex: fitting a screwdriver 12 over the lifting nail 11, turning the screwdriver handle 121 to drive a second travel control body 114 to rotate, and lifting the vertebra through the reaction force with the plate, until each vertebra in the lifting segment fits into the plate body; and
8. inserting a fusion cage or a bone graft in the intervertebral space at head and tail end near the lifting segment outside the lifting segment through the fusion window 4, and performing bone grafting in grooves on both sides of each vertebra in the lifting segment, performing hemostasis, closing the incision, and postoperative braking.

Example 2

Figure 3:
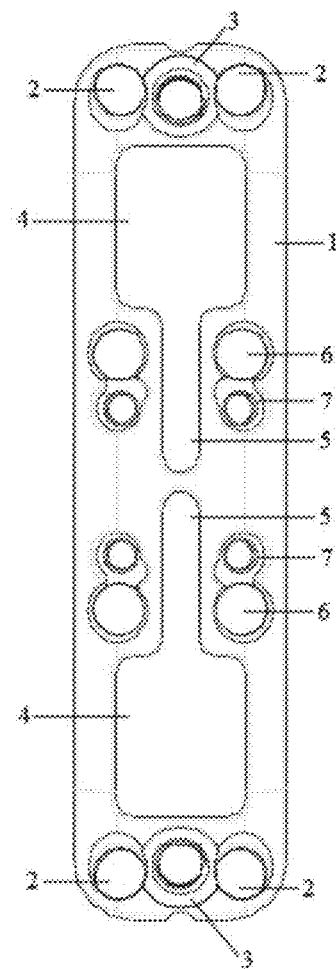
FIG. 3 is a front view of an anterior cervical plate for use in ACAF in a second embodiment of the invention.
Figure 4:
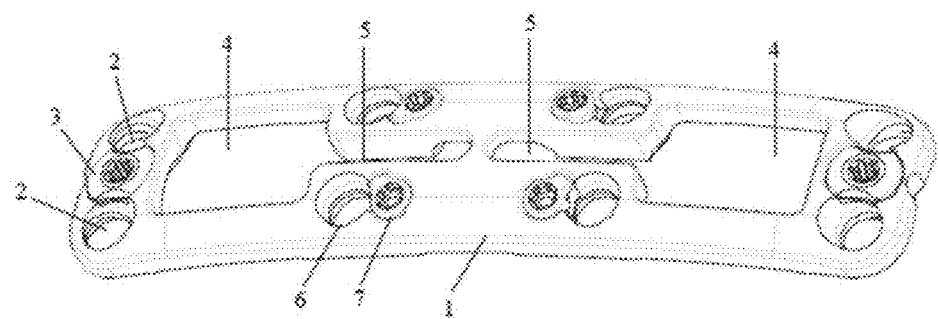
FIG. 4 is a perspective view of the anterior cervical plate for use in ACAF in the second embodiment of the invention.

Referring to FIGS. 3 and 4, FIG. 3 is a front view of an anterior cervical plate for use in ACAF in a second embodiment of the invention, and FIG. 4 is a perspective view of the anterior cervical plate for use in ACAF in the second embodiment of the invention.

The anterior cervical plate for use in ACAF is provided with a plate body 1. The plate body 1 is provided with two end screw fixing holes 2 at its head and tail ends respectively. The two end screw fixing holes 2 are arranged at left and right sides, respectively, and an end screw locking element 3 is provided therebetween. The plate body 1 is further provided with two rectangular fusion windows 4. One of the two fusion windows 4 is located below the end screw fixing hole 2 at the head end of the plate body 1, and the other fusion window 4 is located above the end screw fixing hole 2 at the tail end of the plate body 1. The minimum distance (length) between upper and lower side walls of the fusion window 4 in the vertical axial direction is 10 mm, and the minimum distance (width) between left and right side walls of the fusion window 4 in the horizontal axial direction is 8 mm. The plate body 1 is further provided with two lifting grooves 5. The lifting groove 5 is an elongated groove. A lengthwise direction of the elongated lifting groove is consistent with a lengthwise direction of the plate body 1. The lifting groove 5 has a width in a range from 3 mm to 6 mm, and a length in a range from 10 mm to 20 mm. The lifting groove 5 at the head end communicates with the fusion window 4 at the head end, the lifting groove 5 at the tail end communicates with the fusion window 4 at the tail end, and the two lifting grooves and the two fusion windows form a "工" shape. However, of note, the two lifting grooves 5 do not communicate with each other. Left and right sides of the lifting groove 5 is each provided with a side screw fixing hole 6, and each side screw fixing hole 6 is provided with a side screw locking element 7. The side screw fixing holes 6 and the side screw locking elements 7 on the left and right sides are symmetrically distributed.

The anterior cervical plate for use in ACAF in this example can be customized according to the strength of the plate and a physiological structure of a patient. One example of a specification of the anterior cervical plate is as follows: the plate body 1 has a thickness of 3.5 mm, a length of 75 mm, and a width of 16 mm. A central axis of the end screw fixing hole 2 at the head end is inclined 20° toward the head end, and a central axis of the end screw fixing hole 2 at the tail end is inclined 20° toward the tail end. A central axis of each end screw fixing hole 2 is inclined inwardly by 6°.

The anterior cervical plate for use in ACAF in this embodiment is suitable for the case of lifting two vertebrae.

A method for using the cervical vertebra anterior cervical plate for use in ACAF in this embodiment comprises:

1. preoperative preparation: fully evaluating the frontal and lateral position, hyperextension and flexion position of the cervical spine, and perform tracheal movement training; taking detailed measurements of the ossific mass thickness, anteroposterior diameter of the vertebra, cervical curvature, ossific mass width, intervertebral space height and location of the spinal cord by imaging techniques;
2. a patient is under general anesthesia and he/she is in the supine position; a transverse incision or a longitudinal incision is selected according to the length of the surgical segment and the condition of the patient's neck, and the incision is made to expose relevant vertebrae;
3. treatment of the intervertebral space: for the treatment of intervertebral space in a lifting segment, only posterior longitudinal ligament needs to be exposed, and for the treatment of intervertebral space at head and tail ends, the posterior longitudinal ligament of the intervertebral space is removed to expose endorachis;
4. removing a bone in a front part of the vertebra according to a thickness of the ossific mass measured by imaging techniques;
a thickness of the removed bone at the front part of the vertebra is theoretically the same as a thickness of the ossific mass at the rear part of the vertebra; when the ossification thickness exceeds 6 mm, the lifting distance can be further increased by using a curved titanium plate;
5. slotting opposite sides (the opposite side refers to a side away from a surgeon) of each vertebra in the lifting segment, measuring a size of each intervertebral space according to a trial model, and then placing a prebent anterior cervical plate used in ACAF with an appropriate length on an anterior edge of the vertebra, installing vertebral screws on the end screw fixing holes 2 at the head and tail ends of the plate body 1 at a head and tail vertebra outside of the lifting segment; please note that screw tails of the vertebral screws are screwed until they fit against the plate body 1; in the lifting groove, screwing the lifting nail 11 on a pre-lifted vertebra;
slotting on the opposites is as follows: using the forefoot of the uncinate process as an anatomical landmark of the longitudinal osteotomy, selecting an area at a distance of 1 mm from the ossified material as the slotting boundary, after reaching the cortex of the posterior wall of the vertebra, use a laminectomy rongeur to remove the posterior wall of the remaining vertebra at the bottom of the groove;
6. slotting on the same side (the same side refers to a side close to the surgeon) of each vertebra in the lifting segment in a way as the slotting on the opposite sides, and moving on to the next step after both sides are slotted (as shown in FIG. 12);
7. forward movement of the vertebral ossification complex: fitting a screwdriver 12 over the lifting nail 11, turning the screwdriver handle 121 to drive a second travel control body 114 to rotate, and lifting the vertebra through the reaction force with the plate, until each vertebra in the lifting segment fits into the plate body; and
8. inserting a fusion cage or a bone graft in the intervertebral space at the head and tail ends near the lifting segment outside the lifting segment through the fusion window 4, and performing bone grafting in grooves on both sides of each vertebra in the lifting segment, performing hemostasis, closing the incision, and postoperative braking.

Example 3

Figure 5:
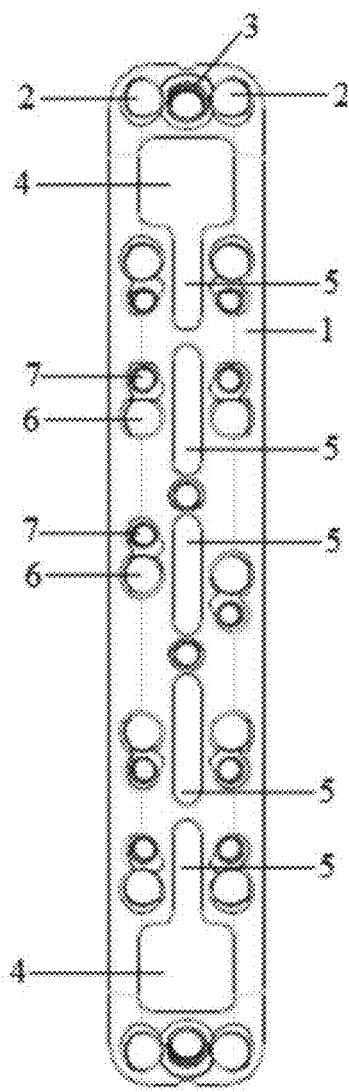
FIG. 5 is a front view of an anterior cervical plate for use in ACAF in a third embodiment of the invention.
Figure 6:
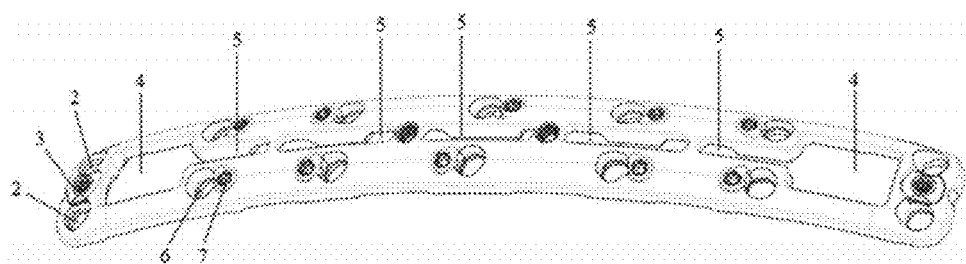
FIG. 6 is a perspective view of the anterior cervical plate for use in ACAF in the third embodiment of the invention.

Referring to FIGS. 5 and 6, FIG. 5 is a front view of an anterior cervical plate for use in ACAF in a third embodiment of the invention, and FIG. 6 is a perspective view of the anterior cervical plate for use in ACAF in the third embodiment of the invention.

The anterior cervical plate for use in ACAF is provided with a plate body 1. The plate body 1 is provided with two end screw fixing holes 2 at its head and tail ends respectively. The two end screw fixing holes 2 are arranged at left and right sides, respectively, and an end screw locking element 3 is provided therebetween. The plate body 1 is further provided with two rectangular fusion windows 4. One of the two fusion windows 4 is located below the end screw fixing hole 2 at the head end of the plate body 1, and the other fusion window 4 is located above the end screw fixing hole 2 at the tail end of the plate body 1. The minimum distance (length) between upper and lower side walls of the fusion window 4 in the vertical axial direction is 10 mm, and the minimum distance (width) between left and right side walls of the fusion window 4 in the horizontal axial direction is 8 mm. The plate body 1 is further provided with five lifting grooves 5. The lifting groove 5 is an elongated groove. A lengthwise direction of the elongated lifting groove is consistent with a lengthwise direction of the plate body 1. The lifting groove 5 has a width in a range from 3 mm to 6 mm, and a length in a range from 10 mm to 20 mm. The five lifting grooves 5 are arranged on the plate body 1 in a vertical axis direction, wherein the lifting groove 5 at the head end communicates with the fusion window 4 at the head end, the lifting groove 5 at the tail end communicates with the fusion window 4 at the tail end, the lifting grooves 5 and the fusion windows 4 form a "⊥" shape. However, adjacent lifting grooves 5 do not communicate with each other. Left and right sides of the lifting groove 5 is each provided with a side screw fixing hole 6, and each side screw fixing hole 6 is provided with a side screw locking element 7. The side screw fixing holes 6 and the side screw locking elements 7 on the left and right sides are symmetrically distributed.

The anterior cervical plate for use in ACAF in this example can be customized according to the strength of the plate and a physiological structure of a patient. One example of a specification of the anterior cervical plate is as follows: the plate body 1 has a thickness of 3.5 mm, a length of 147 mm, and a width of 16 mm. A central axis of the end screw fixing hole 2 at the head end is inclined 20° toward the head end, and a central axis of the end screw fixing hole 2 at the tail end is inclined 20° toward the tail end. A central axis of each end screw fixing hole 2 is inclined inwardly by 6°.

The anterior cervical plate for use in ACAF in this embodiment is suitable for the case of lifting five vertebrae.

A method for using the anterior cervical plate for use in ACAF in this embodiment comprises;
1. preoperative preparation: fully evaluating the frontal and lateral position, hyperextension and flexion position of the cervical spine, and perform tracheal movement training; taking detailed measurements of the ossific mass thickness, anteroposterior diameter of the vertebra, cervical curvature, ossific mass width, intervertebral space height and location of the spinal cord by imaging techniques;

2. a patient is under general anesthesia and he/she is in the supine position; a transverse incision or a longitudinal incision is selected according to the length of the surgical segment and the condition of the patient's neck, and the incision is made to expose relevant vertebrae;
3. treatment of the intervertebral space: for the treatment of intervertebral space in a lifting segment, only posterior longitudinal ligament needs to be exposed, and for the treatment of intervertebral space at head and tail ends, the posterior longitudinal ligament of the intervertebral space is removed to expose endorachis;
4. removing a bone in a front part of the vertebra according to a thickness of the ossific mass measured by imaging techniques;
a thickness of the removed bone at the front part of the vertebra is theoretically the same as a thickness of the ossific mass at the rear part of the vertebra; when the ossification thickness exceeds 6 mm, the lifting distance can be further increased by using a curved titanium plate;
5. slotting opposite sides (the opposite side refers to a side away from a surgeon) of each vertebra in the lifting segment, measuring a size of each intervertebral space according to a trial model, installing the cervical fusion cage in the intervertebral space between the lifting segments; and then placing a prebent anterior cervical plate used in ACAF with an appropriate length on an anterior edge of the vertebra, installing vertebral screws on the end screw fixing holes 2 at the head and tail ends of the plate body 1 at a head and tail vertebra outside of the lifting segment; please note that screw tails of the vertebral screws are screwed until they fit against the plate body 1; in the lifting groove, screwing the lifting nail 11 on a pre-lifted vertebra;
slotting on the opposites is as follows: using the forefoot of the uncinate process as an anatomical landmark of the longitudinal osteotomy, selecting an area at a distance of 1 mm from the ossified material as the slotting boundary, after reaching the cortex of the posterior wall of the vertebra, use a laminectomy rongeur to remove the posterior wall of the remaining vertebra at the bottom of the groove;
6. slotting on the same side (the same side refers to a side close to the surgeon) of each vertebra in the lifting segment in a way as the slotting on the opposite sides, and moving on to the next step after both sides are slotted (as shown in FIG. 12);
7. forward movement of the vertebral ossification complex: fitting a screwdriver 12 over the lifting nail 11, turning the screwdriver handle 121 to drive a second travel control body 114 to rotate, and lifting the vertebra through the reaction force with the plate, until each vertebra in the lifting segment fits into the plate body; and
8. inserting a fusion cage or a bone graft in the intervertebral space at the head and tail ends near the lifting segment outside the lifting segment through the fusion window 4, and performing bone grafting in grooves on both sides of each vertebra in the lifting segment, performing hemostasis, closing the incision, and postoperative braking.

Example 4

Figure 7:
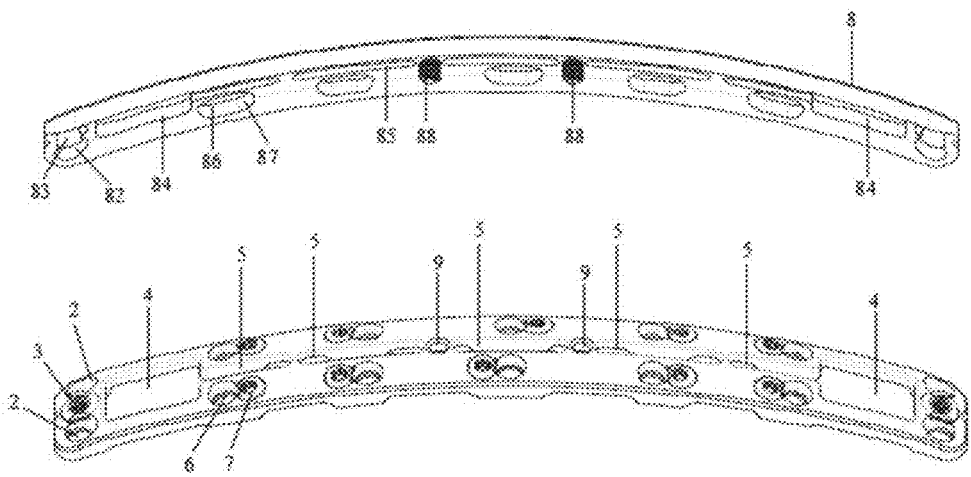
FIG. 7 is a schematic view showing a structure of an anterior cervical plate for use in ACAF in a fourth embodiment of the invention.
Figure 8:
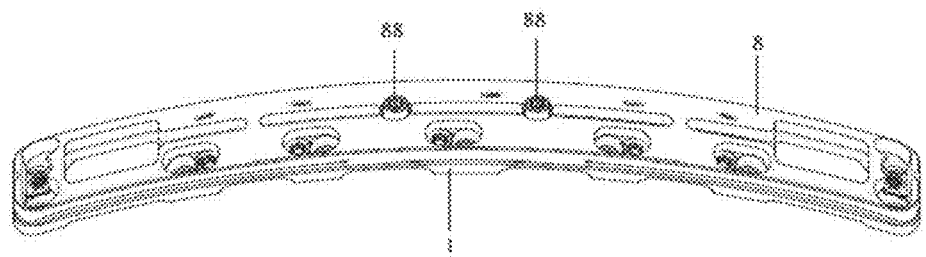
FIG. 8 is a view showing the status of the anterior cervical plate for use in ACAF in the fourth embodiment of the invention when it is in use.

Referring to FIGS. 7 and 8, FIG. 7 is a schematic view showing a structure of an anterior cervical plate for use in ACAF in a fourth embodiment of the invention, and FIG. 8 is a view showing the status of the anterior cervical plate for use in ACAF in the fourth embodiment of the invention when it is in use.

The anterior cervical plate for use in ACAF is provided with a plate body 1. The plate body 1 is provided with two end screw fixing holes 2 at its head and tail ends. The two end screw fixing holes 2 are arranged at left and right sides, respectively, and an end screw locking element 3 is provided therebetween. The plate body 1 is further provided with two rectangular fusion windows 4. One of the two fusion windows 4 is located below the end screw fixing hole 2 at the head end of the plate body 1, and the other fusion window 4 is located above the end screw fixing hole 2 at the tail end of the plate body 1. The minimum distance (length) between upper and lower side walls of the fusion window 4 in the vertical axial direction is 10 mm, and the minimum distance (width) between left and right side walls of the fusion window 4 in the horizontal axial direction is 8 mm. The plate body 1 is further provided with five lifting grooves 5. The lifting groove 5 is an elongated groove. A lengthwise direction of the elongated lifting groove is consistent with a lengthwise direction of the plate body 1. The lifting groove 5 has a width in a range from 3 mm to 6 mm, and a length in a range from 10 mm to 20 mm. The lifting groove 5 at the head end communicates with the fusion window 4 at the head end, the lifting groove 5 at the tail end communicates with the fusion window 4 at the tail end, the five lifting grooves 5 and the two fusion windows 4 form a " 工 " shape. However, adjacent lifting grooves 5 do not communicate with each other. Left and right sides of the lifting groove 5 is each provided with a side screw fixing hole 6, and each side screw fixing hole 6 is provided with a side screw locking element 7. The side screw fixing holes 6 and the side screw locking elements 7 on the left and right sides are symmetrically distributed. The anterior cervical plate for use in ACAF is further provided with an auxiliary plate 8. The auxiliary plate 8 has the same shape as the plate body 1. The auxiliary plate 8 is provided with an end screw fixing hole viewing window 82 at a position which corresponds to each end screw fixing hole 2 of the plate body 1. The auxiliary plate 8 is provided with an end screw locking element viewing window 83 at a position which corresponds to each end screw locking element 3 of the plate body 1. The auxiliary plate 8 is provided with a fusion window viewing window 84 at a position which corresponds to each fusion window 4 of the plate body 1. The auxiliary plate 8 is provided with a lifting groove viewing window 85 at a position which corresponds to each lifting groove 5 of the plate body 1. The auxiliary plate 8 is provided with a side screw fixing hole viewing window 86 at a position which corresponds to each side screw fixing hole 6 of the plate body 1. The auxiliary plate 8 is provided with a side screw locking element viewing window 87 at a position which corresponds to each side screw locking element 7 of the plate body 1, and each side screw fixing hole viewing window 86 is integral with the side screw locking element viewing window 87 to which it corresponds. The auxiliary plate 8 is further provided with a second locking element 88. The second locking element 88 is mainly in the form of two threaded locks. The two thread locks correspond to the first locking element 9 on the plate body 1 respectively when in use, and the first locking element 9 is two threaded holes.

The anterior cervical plate for use in ACAF in this example can be customized according to the strength of the plate and a physiological structure of a patient. One example of a specification of the anterior cervical plate is as follows:

the plate body 1 has a thickness of 3.5 mm, a length of 147 mm, and a width of 16 mm. A central axis of the end screw fixing hole 2 at the head end is inclined 20° toward the head end, and a central axis of the end screw fixing hole 2 at the tail end is inclined 20° toward the tail end. A central axis of each end screw fixing hole 2 is inclined inwardly by 6°. The auxiliary plate 8 has a thickness of 3.5 mm, a length of 147 mm, and a width of 16 mm.

The anterior cervical plate for use in ACAF in this embodiment is suitable for the case of lifting five vertebrae.

A method for using the anterior cervical plate for use in ACAF in this embodiment comprises:

1. preoperative preparation: fully evaluating the frontal and lateral position, hyperextension and flexion position of the cervical spine, and perform tracheal movement training; taking detailed measurements of the ossific mass thickness, anteroposterior diameter of the vertebra, cervical curvature, ossific mass width, intervertebral space height and location of the spinal cord by imaging techniques;
2. a patient is under general anesthesia and he/she is in the supine position; a transverse incision or a longitudinal incision is selected according to the length of the surgical segment and the condition of the patient's neck, and the incision is made to expose relevant vertebrae;
3. treatment of the intervertebral space: for the treatment of intervertebral space in a lifting segment, only posterior longitudinal ligament needs to be exposed, and for the treatment of intervertebral space at head and tail ends, the posterior longitudinal ligament of the intervertebral space is removed to expose endorachis;
4. removing a bone in a front part of the vertebra according to a thickness of the ossific mass measured by imaging techniques;
a thickness of the removed bone at the front part of the vertebra is theoretically the same as a thickness of the ossific mass at the rear part of the vertebra; when the ossification thickness exceeds 6 mm, the lifting distance can be further increased by using a curved titanium plate;
5. slotting opposite sides (the opposite side refers to a side away from a surgeon) of each vertebra in the lifting segment, measuring a size of each intervertebral space according to a trial model, installing the cervical fusion cage in the intervertebral space between the lifting segments; and then placing a prebent anterior cervical plate used in ACAF with an appropriate length on an anterior edge of the vertebra, installing vertebral screws on the end screw fixing holes 2 at the head and tail ends of the plate body 1 at a head and tail vertebra outside of the lifting segment; please note that screw tails of the vertebral screws are screwed until they fit against the plate body 1; in the lifting groove, screwing the lifting nail 11 on a pre-lifted vertebra;
slotting on the opposites is as follows: using the forefoot of the uncinate process as an anatomical landmark of the longitudinal osteotomy, selecting an area at a distance of 1 mm from the ossified material as the slotting boundary, after reaching the cortex of the posterior wall of the vertebra, use a laminectomy rongeur to remove the posterior wall of the remaining vertebra at the bottom of the groove;
6. slotting on the same side (the same side refers to a side close to the surgeon) of each vertebra in the lifting segment in a way as the slotting on the opposite sides, and moving on to the next step after both sides are slotted (as shown in FIG. 12);
7. the auxiliary plate 8 is fitted onto the plate body 1 with the first locking element 9 and the second locking element 88, and the auxiliary plate 8 is fixedly fastened to the plate body 1;
8. forward movement of the vertebral ossification complex: fitting a screwdriver 12 over the lifting nail 11, turning the screwdriver handle 121 to drive a second travel control body 114 to rotate, and lifting the vertebra through the reaction force with the plate, until each vertebra in the lifting segment fits into the plate body;
9. removing the auxiliary plate 8; and
10. inserting a fusion cage or a bone graft in the intervertebral space at the head and tail ends near the lifting segment outside the lifting segment through the fusion window 4, and performing bone grafting in grooves on both sides of each vertebra in the lifting segment, performing hemostasis, closing the incision, and postoperative braking.

Figure 11:
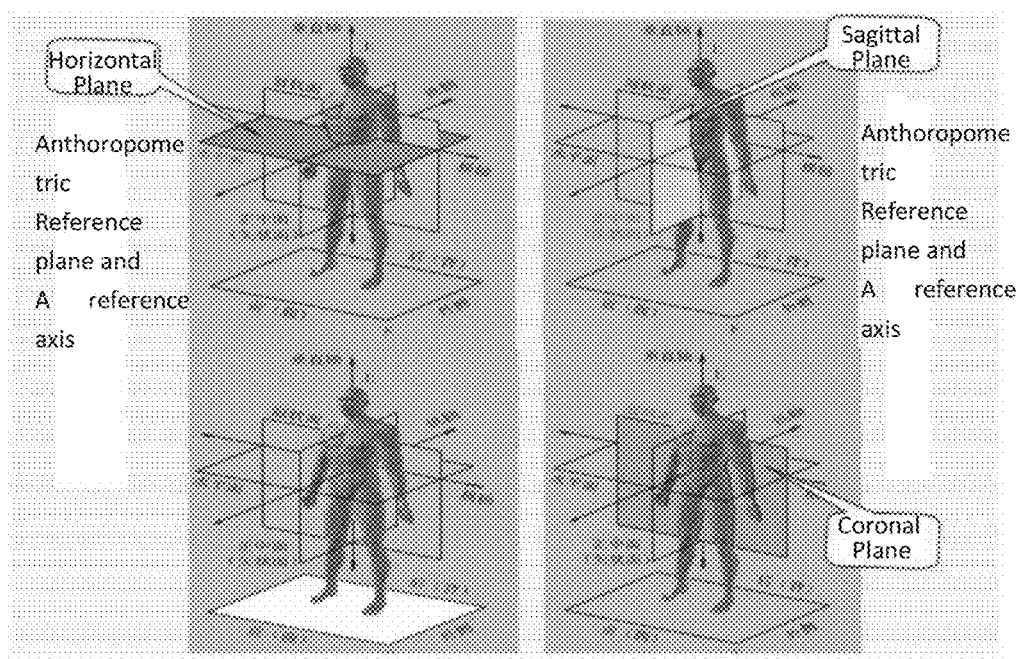
FIG. 11 is a schematic view of an anthropometric reference plane and a reference axis.

For the above-mentioned Examples 1-4, it should be noted that:

Herein, the terms "vertical axis". "longitudinal axis". "horizontal axis", "coronal plane", "horizontal plane", "sagittal plane" are defined in terms of an anthropometric reference plane and a reference axis, see FIG. 11. The terms "head", "tail", "upper", "lower", "left" and "right" indicate orientations based on the viewing angle of the device of the present invention when in use. The terms "first" and "second" are used for descriptive purposes only and should not be construed to indicate or imply relative importance.

For the anterior cervical plate for use in ACAF in the present invention, fusion windows 4 are provided at the head end and the tail end of the plate body 1, and the size of each fusion window 4 is large, allowing an intervertebral fusion cage (10 mm*5-8 mm) to be placed into the window after the plate is fixed. When compared with the current anterior cervical plate in clinical use, the plate can be placed and fixed first, and the lifting operation can be performed. After the lifting operation is completed and the plate is fixed, the fusion cage or the bone graft is arranged in place through the fusion windows on both sides. In this way, the following problems can be avoided; the vertebra is clamped with the remaining vertebra after the placement of the fusion cage in the operation sequence of the prior art, which will affect the subsequent forward movement operation, resulting in the obstruction of the advancement of the cervical vertebra and the compression object; the physiological curvature of the cervical spine is not well restored, and the physiological curvature is difficult to restore during the operation, or the physiological curvature is lost after the operation. The lifting groove 5 is an elongated groove along the vertical axis direction, that is, in a longitudinal axis direction of the plate body 1, and is located at the center of the longitudinal axis of the plate body 1, allowing the lifter to pass through, ensuring lifting of each vertebra is completed at the center of the vertebra. As a result, rotation of the vertebra during the lifting process can be avoided. The position of the lifting tool can be flexibly determined according to the size of the vertebra and intervertebral disc of different patients, so it can achieve a precise and controllable decompression and significantly reduce the occurrence of complications such as nerve root pain. The fusion windows 4 are only arranged at the head end and the tail end for the placement of the fusion cage in the intervertebral space at the head end and the tail end outside of the lifting segment. The fusion cage or the bone graft is first placed into the intervertebral space in the lifting segment, since it is found in the clinic practice that the vertebrae of the lifting segment have been in a free state. Therefore, when the fusion cage or the bone graft is first placed into the intervertebral space followed by the lifting operation, due to the fact that each vertebra has a certain degree of freedom, precise lifting of the vertebra may not be affected, and this design ensures the strength of the plate. The fusion window 4 communicates with its adjacent lifting groove 5, because the fusion window is the position of the intervertebral space, and the vertebral body end plate is arranged in a direction of the central position, and the position of the vertebra close to the end plate has higher strength. The stronger the holding force of the lifting nail, the stronger the lifting force. In such a design where the fusion windows communicate with the lifting groove, it is convenient to place the lifting nail in the best place. For the case where the number of the lifting grooves 5 is two or more, the lifting grooves 5 do not communicate with to each other. In fact, the lifting grooves should be designed as a whole, which is convenient to freely choose the best place for the lifting nail. For the long plate, the lifting groove with a length corresponding to a length of the plate will affect the strength of the plate.

Therefore, according to mechanical mechanics, without affecting the placement of the lifting nails, several intervals are arranged, and the design of the intervals are intended to increase the mechanical strength of the plate. The space is located at a position where the fusion of the intervertebral space occurs. The placement of the intervals does not affect the free placement of the lifting nails. The auxiliary plate 8 is beneficial to increase the strength of the plate during the operation, and can obviously and reliably restore the overall physiological curvature of the cervical spine during the operation and after the operation. The auxiliary steel plate 8 preferably has the same shape as the plate body 1, which can fully cover the plate body 1, buffer the force received by the plate body 1 during the fixing process or the vertebra lifting process, and protect each part of the plate body 1. The side screw fixing holes 6 and the side screw locking elements 7 on the left and right sides of the lifting groove 5 are symmetrically arranged. The screw fixing holes and the lifting nails are symmetrically arranged so that holding strength of the nails can be increased, and maximum lifting and fixing strength is obtained.

The shape of the fusion window 4 of the present invention is not limited to a rectangle, but other shapes can also be contemplated, such as an ellipse, a circle, and a square. The lifting groove 5 preferably has a width in a range from 3 mm to 6 mm, a length in a range from 10 mm to 20 mm. During the operation, the auxiliary plate 8 and the plate body 1 need to be fixed, the ways of fixing are not limited by snap-proof rotation, screw tightening, and riveting. The plate body 1 can be made of any material that meets clinical vertebra fixation strength and safety requirements, such as stainless steel, silicon steel, carbon steel, titanium alloy, pure titanium, cobalt-nickel alloy, polymer materials, and the like. Anti-slip textures, such as anti-slip particles, water ripples, can be formed on a surface of the plate body 1. The anterior cervical plate for use in ACAF in the present invention is not only suitable for the ACAF operation to treat various types of OPLL diseases of the cervical spine, but also can be routinely used for the surgical treatment of cervical spine degeneration, fractures, tumors and other diseases.

Example 5

Figure 9:
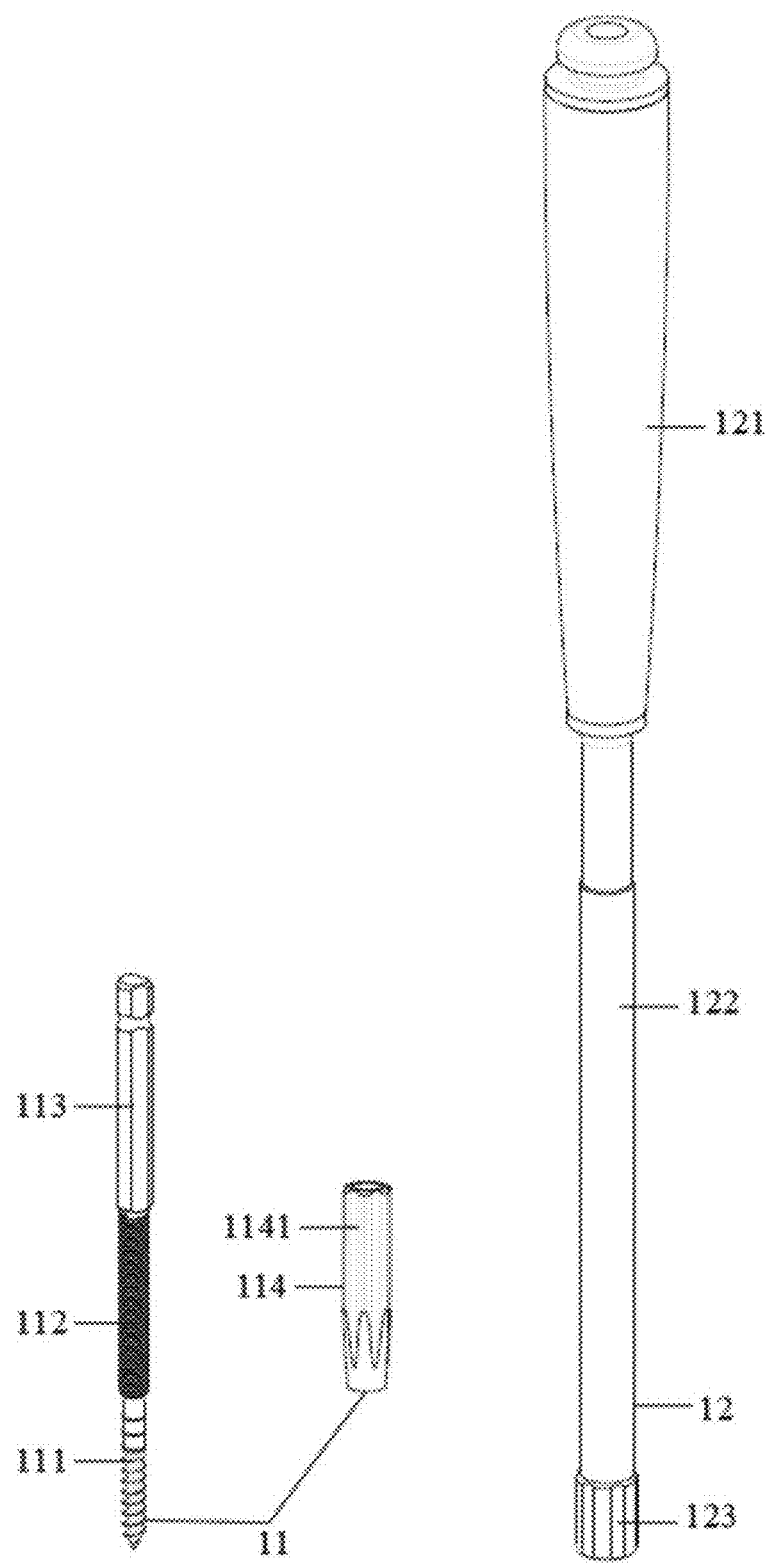
FIG. 9 is one of the schematic views of the structure of a lifter for use in ACAF in a fifth embodiment of the invention.
Figure 10:
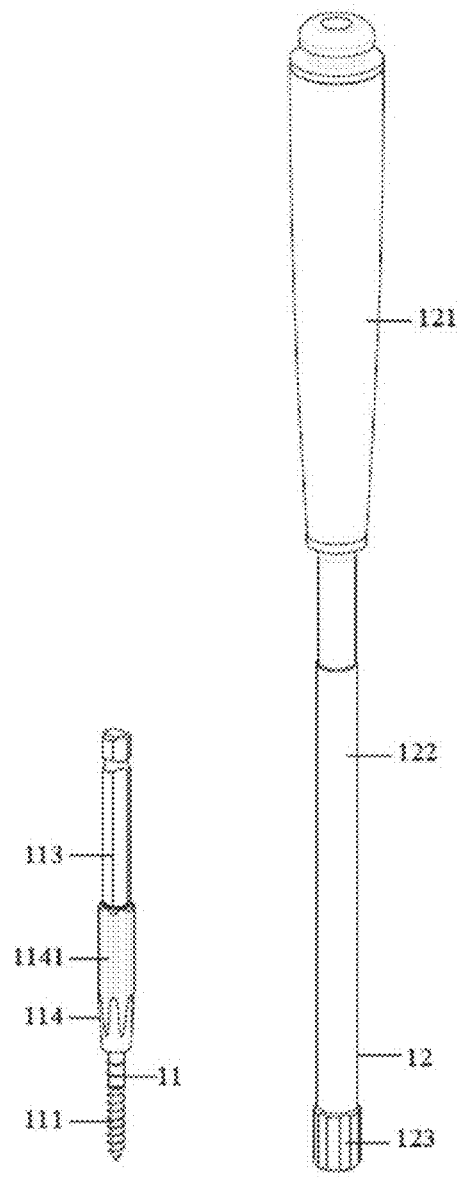
FIG. 10 is another schematic view of the structure of a lifter for use in ACAF in the fifth embodiment of the invention

Referring to FIGS. 9 and 10, FIG. 9 is one of the schematic views of a structure of a lifter for use in ACAF in a fifth embodiment of the invention, and FIG. 10 is another schematic view of a structure of a lifter for use in ACAF in the fifth embodiment of the invention. The lifter comprises a lifting nail 11 and a screwdriver 12. The lifting nail 11 is provided with a lifting fixation body 111, a first travel control body 112, a mounting joint 113 and a second travel control body 114. One end of the first travel control body 112 is connected to the lifting fixation body 111, the other end of the first travel control body 112 is connected to the mounting joint 113, the first travel control body 112 is provided with an external thread. The second travel control body 114 is sleeved outside of the first travel control body 112 and is provided with an internal thread matching with an external thread of the first travel control body 112. When the internal thread on the second travel control body 114 and the external thread on the first travel control body 112 are screwed together, relative motions are generated between the first travel control body 112 and the second travel control body 114, and the first travel control body 112 and the second control body 114 are moving in the same axial direction. An axial groove 1141 is molded on an outer surface of the second travel control body 114. The screwdriver 12 is provided with a screwdriver handle 121, a screwdriver extension rod 122 and a screwdriver sleeve head 123. A lower end of the screwdriver extension rod 122 and the screwdriver sleeve head 123 are hollow. An interior of the screwdriver sleeve head 123 is provided with a groove matched with the groove 1141 on the second travel control body 114. An inner diameter of the screwdriver extension rod 122 is equal to the maximum outer diameter of the second travel control body 114.

A method for using the lifter in ACAF is as follows: a socket screwdriver matching the mounting joint 113 of the lifting nail 11 is used to implant the lifting fixation body 111 of the lifting nail 11 into the vertebra to be lifted along a lifting groove of the plate, then the socket screwdriver is removed, the implantation depth is confirmed by fluoroscopy, and then the screwdriver 12 is inserted along the top of the lifting nail 11, and after the implanting the second travel control body 114 of the lifting nail 11 just corresponds to the position of the screwdriver sleeve head 123, and the grooves of the screwdriver sleeve head 123 and the lifting nail 11 are matched and engaged. Rotating the screwdriver handle 121 to drive the second travel control body 114 to rotate, and the vertebra is lifted by the reaction force with the plate.

The lifter for use in ACAF in the present invention comprises two separable parts: a lifting nail 11 and a screwdriver 12. The longer screwdriver 12 drives the second travel control body 114 to lift the vertebra. When compared with a process in which the vertebra is lifted by directly rotating the second travel control body 114, the second travel control body 114 is more uniform in stress. In this way, the vertebra can be stably lifted under the effect of a more uniform force, and force applied to the plate is also more uniform, so that relative twisting of the plate relative to the vertebra at the head and tail ends outside of the lifting segment can be effectively avoided. Then damage to the vertebra from the surgery can be avoided, to the greatest extent.

Example 6

The internal fixation system for use in ACAF in the present invention comprises the anterior cervical plate for use in ACAF of any one of Examples 1-4 and the lifter for use in ACAF of Example 5, wherein a maximum outer diameter of the lifting fixation body of the lifter is less than a width of the lifting groove of the anterior cervical plate. With the aid of the anterior cervical plate and the lifter, a precise, controllable, stable and safe lifting of the vertebra can be realized, to the greatest extent, and the surgical effect of the ACAF surgery is greatly improved.

The above descriptions are only the preferred embodiments of the invention, not thus limiting the embodiments and scope of the invention. Those skilled in the art should be able to realize that the schemes obtained from the content of specification and drawings of the invention are within the scope of the invention.

What is claimed is:

1. An internal fixation system for use in anterior controllable antedisplacement and fusion (ACAF), comprising an anterior cervical plate for use in ACAF and a lifter;
wherein the anterior cervical plate for use in ACAF has a plate body and a screw fixing hole, fusion windows are formed at a head end and a tail end of the plate body, each of the fusion windows has a width of more than 8 mm, and a height of more than 10 mm; at least one elongated lifting groove is provided at a central longitudinal axis of the plate body, a lengthwise direction of the at least one elongated lifting groove is consistent with a lengthwise direction of the plate body;
wherein the lifter comprises a lifting nail and a screwdriver; the lifting nail is provided with a lifting fixation body, a first travel control body, a mounting joint and a second travel control body, the second travel control body is sleeved outside of the first travel control body, and the second travel control body is provided with an internal thread matching with an external thread of the first travel control body, an axial groove is molded on an outer surface of the second travel control body; the screwdriver is provided with a screwdriver handle, a screwdriver extension rod and a screwdriver sleeve head, an interior of the screwdriver sleeve head is provided with an groove matching with the groove of the second travel control body.

2. An application of the internal fixation system for use in ACAF of claim 1, comprising the steps of:
Step 1, preoperative preparation, including measuring a thickness of an ossific mass;
Step 2, making an incision according to the length of a surgical segment and the condition of a patient's neck to expose relevant vertebral bodies;
Step 3, exposing posterior longitudinal ligament in a treatment of intervertebral space within lifting segment; and removing posterior longitudinal ligament of intervertebral space to expose dura mater in a treatment of the intervertebral space at head end and tail end of lifting segment;
Step 4, removing a bone in a front part of the vertebra according to a thickness of the ossific mass of each segment;
Step 5, slotting opposite sides of each vertebra in the lifting segment, and then pre-bending and placing the anterior cervical plate used in ACAF with an appropriate length on an anterior edge of the vertebra, installing vertebral screws on the end screw fixing holes at the head and tail ends of the plate body at a head and tail vertebra outside of the lifting segment; in the lifting groove, screwing the lifting nail on a pre-lifted vertebra;
Step 6, slotting on the same side of each vertebra in the lifting segment;
Step 7, fitting the screwdriver over the lifting nail, turning the screwdriver handle until each vertebra in the lifting segment fits into the plate body; and
Step 8, inserting a fusion cage or a bone graft in the intervertebral space at the head and tail ends of a portion, which is adjacent to the lifting segment, through each of the fusion windows, and performing bone grafting in grooves on both sides of each vertebra in the lifting segment, performing hemostasis, closing the incision, and postoperative braking.

3. The internal fixation system for use in ACAF of claim 1, wherein the anterior cervical plate for use in ACAF further comprises an auxiliary plate, the auxiliary plate covers a front side of the plate body when in use and exposes to the fusion windows, the lifting groove of the plate body, and the screw fixing hole, and the auxiliary plate is fixed to the plate body.

4. The internal fixation system for use in ACAF of claim 1, wherein the auxiliary plate is fixed to the plate body with screw, with bayonet, or by riveting; the auxiliary plate has the same shape as the plate body.

5. The internal fixation system for use in ACAF of claim 1, wherein the number of the lifting groove is 1, the fusion window at the head end, the fusion window at the tail end and the lifting groove are in communication with one another.

6. The internal fixation system for use in ACAF of claim 1, wherein the number of the lifting groove is 2 or greater than 2, the fusion window at the head end communicates with a lifting groove close to the head end, the fusion window at the tail end communicates with a lifting groove close to the tail end, and the lifting grooves do not communicate with each other.

7. The internal fixation system for use in ACAF of claim 1, wherein the screw fixing hole comprises an end screw fixing hole and a side screw fixing hole, the end screw fixing hole is located at the head and tail ends of the plate body, the side screw fixing hole is located on left and right sides of the lifting groove.

8. The internal fixation system for use in ACAF of claim 1, wherein the fusion window at the head end is located below the end screw fixing hole at the head end, and the fusion window at the tail end is located above the end screw fixing hole at the tail end.

9. The internal fixation system for use in ACAF of claim 1, wherein the plate body is made of stainless steel, silicon steel, carbon steel, titanium alloy, pure titanium, cobalt-nickel alloy or a polymer material.

* * * * *